US00PP09451P

United States Patent [19]

VandenBerg

[11] Patent Number: Plant 9,451

[45] Date of Patent: Feb. 13, 1996

[54] CHRYSANTHEMUM PLANT NAMED 'ORANGE BLUSH'

[75] Inventor: Cornelis P. VandenBerg, Salinas, Calif.

[73] Assignee: Yoder Brothers, Inc., Barberton, Ohio

[21] Appl. No.: 331,856

[22] Filed: Nov. 1, 1994

[51] Int. Cl.[6] ..... A01H 5/00

[52] U.S. Cl. ..... Plt./82.2

[58] Field of Search ..... Plt./82.2, 82.3

[56] References Cited

U.S. PATENT DOCUMENTS

| | | | |
|---|---|---|---|
| P.P. 7,469 | 3/1991 | VandenBerg | Plt./82.2 |
| P.P. 8,474 | 11/1993 | VandenBerg | Plt./82.2 |
| 4,616,099 | 10/1986 | Sparkes | 47/58 |

OTHER PUBLICATIONS

Chan, 1966, "Chrysanthemum and rose mutations induced by X-rays", Am. Soc. Hort. Sci., vol. 88, pp. 613–620.

Broertjes, 1966, "Mutation breeding of chrysanthemums", Euphytica 15:156–167.

Dowrick, et al., 1966, "The induction of mutations in chrysanthemum using X-and gamma radiation", Euphytica, 15:204–210.

Broertjes, et al. 1980, "A mutant of a mutant of a . . . Irradiation of progressive radiation–induced mutants in a mutation breeding programme with *Chrysanthemum morifolium*", Euphytica 29:525–530.

Gosling, ed., 1979, "The Chrysanthemum Manual–6th edition", The National Chrysanthemum Socity, Essex Telegraph Press, Ltd., London, pp. 329–336.

Broertjes, et al., 1978, "Application of Mutation Breeding Methods in the Improvement of Vegetatively Propagated Crops", Elsevier Sci. Pub. Co. New York, pp. 162–175.

Searle, et al., 1968, "Chrysanthemums the Year Round"–3rd edition, Blanford Press, London, pp. 27–29, 320–327.

*Primary Examiner*—Howard J. Locker

*Attorney, Agent, or Firm*—Foley & Lardner

[57] ABSTRACT

A Chrysanthemum plant named Orange Blush particularly characterized by its flat capitulum form; daisy capitulum type; orange-bronze ray floret color; diameter across face of capitulum of 117 to 133 mm when fully opened, when grown as a pinched disbudded pot mum; photoperiodic flowering response to short days of 49 to 55 days; plant height, with 20 to 22 long days after sticking unrooted cuttings and with 1 to 2 applications of 2500 ppm B-9 SP, ranges from 23 to 28 cm when grown as a pinched pot mum with 4 cuttings in a 15 cm pot; branching pattern is semi-spreading, each plant having 3 to 5 laterals after pinch; and recommended as disbudded pot mum.

1 Drawing Sheet

The present invention comprises a new and distinct cultivar of Chrysanthemum, botanically known as *Dendranthema grandiflora*, and referred to by the cultivar name Orange Blush.

Orange Blush, identified as 5684 (86-627F02), is a product of a mutation induction program. The new cultivar was discovered and selected by Cornelis P. VandenBerg on Jul. 23, 1990 in a controlled environment in Salinas, Calif., as one flowering plant within a flowering block established as rooted cuttings from stock plants which had been exposed as unrooted cuttings to an X-ray source of 1750 rads in Fort Myers, Fla., on Feb. 8, 1990. The irradiated parent cultivar was the cultivar identified as Blush, disclosed in U.S. Plant Pat. No. 7,985, and described as a disbud daisy pot mum with a flat capitulum form; soft pink ray floret color; diameter across face of capitulum of 114 to 140 mm when fully opened, when grown as a pinched disbudded pot mum; flowering response period of 47 to 55 days after start of short days; plant height of 23 to 28 cm with 1 to 3 applications of 2500 ppm B-9 SP when grown as a pinched pot mum in a 15 cm pot; semi-spreading branching pattern, with 3 to 5 laterals after pinch; and recommended as a disbudded pot mum. The description of Blush has a wider range of measurements than the patented description of Blush, based on continued flowering trials of Blush after filing the plant patent application for Blush.

The irradiation program resulting in Orange Blush had as its primary objective the expansion of color ranges of the parent cultivar Blush. The irradiation program comprised irradiating cuttings of the parent cultivar at irradiation levels of 1500, 1750 and 2000 rads. A total of 1433 cuttings harvested from a total of 225 irradiated plants were planted on May 28, May 21 and May 14, 1990, respectively. Of these, 19 initial selections were made, which selections were then revegetated and reflowered. Three consecutive flowerings resulted in discarding 12 of the original 19 selections on Apr. 23, 1991. Seven selections were retained and given PI (Possible Introduction) status. Continued flowering trials resulted in discarding 3 of the 7 remaining selections. The remaining selections were designated White Blush, Coral Blush, Orange Blush and Pink Blush. All four selections were introduced in Europe at the same time, and White Blush and Coral Blush were introduced in the United States at that time. Pink Blush and Orange Blush were introduced in the United States one year after introduction in Europe. The selections White Blush, Coral Blush, and Pink Blush are disclosed in pending application Ser. Nos. 08/296,467, 08/296,466 and 08/331,863, respectively.

The first act of asexual reproduction of Orange Blush was accomplished when vegetative cuttings were taken from the initial selection in September 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Orange Blush are firmly fixed and are retained through successive generations of asexual reproduction.

Orange Blush has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Orange Blush, which, in combination, distinguish this Chrysanthemum as a new and distinct cultivar:

1. Flat capitulum form.
2. Daisy capitulum type.
3. Orange-bronze ray floret color.
4. Diameter across face of capitulum of 117 to 133 mm when fully opened, when grown as pinched disbudded pot mum.
5. Photoperiodic flowering response to short days of 49 to 55 days.
6. Plant height, with 20 to 22 long days after sticking unrooted cuttings and with 1 to 2 applications of 2500 ppm B-9 SP, ranges from 23 to 28 cm when grown as a pinched pot mum with 4 cuttings in a 15 cm pot.
7. Branching pattern is semi-spreading, each plant having 3 to 5 laterals after pinch.
8. Recommended as disbudded pot mum.

The accompanying photographic drawing is a side view of a potted mum of Orange Blush, with 4 cuttings in a 15 cm pot, with the colors being as nearly true as possible with illustrations of this type.

Of the commercial cultivars known to the inventor, the most similar in comparison to Orange Blush is the parent cultivar Blush. All traits of Orange Blush are similar to those of Blush, except for ray floret color and the diameter of capitulum. The ray floret color of Orange Blush is orange-bronze, while the ray floret color of Blush is soft pink. The diameter of capitulum of Orange Blush has been slightly smaller than the diameter of capitulum of Blush.

In the following description, color references are made to The Royal Horticultural Society Colour Chart. The color values were determined on plant material grown as a pinched disbudded pot mum in Salinas, Calif. on Feb. 25, 1993.

Classification:

*Botanical.*—*Dendranthema grandiflora* cv Orange Blush.

*Commercial.*—Flat daisy disbud pot mum.

INFLORESCENCE

A. Capitulum:

*Form.*—Flat

*Type.*—Daisy.

*Diameter across face.*—117 to 133 mm when fully opened.

B. Corolla of ray florets:

*Color (general tonality from a distance of three meters).*—Orange-bronze.

*Color (upper surface).*—16A, slightly streaked with 26B.

*Color (under surface).*—11A, overcast with 13C.

*Shape.*—Straight, pointed, slightly ribbed.

C. Corolla of disc florets:

*Color (mature).*—7B.

*Color (immature).*—144A to 144B.

D. Reproductive organs:

*Androecium.*—Present on disc florets only; scant pollen.

*Gynoecium.*—Present on both ray and disc florets.

PLANT

A. General appearance:

*Height.*—23 to 28 cm when grown as a pinched pot mum with 20 to 22 long days prior to start of short days, and with 1 to 2 applications of 2500 ppm B-9 SP.

*Branching pattern.*—Semi-spreading, with 3 to 5 laterals after pinch.

B. Foliage:

*Color (upper surface).*—147A.

*Color (under surface).*—147B.

*Shape.*—Deeply lobed and slightly serrated.

*Size.*—75–85 mm in length and 45–50 mm in width.

I claim:

1. A new and distinct Chrysanthemum plant named Orange Blush, as described and illustrated.

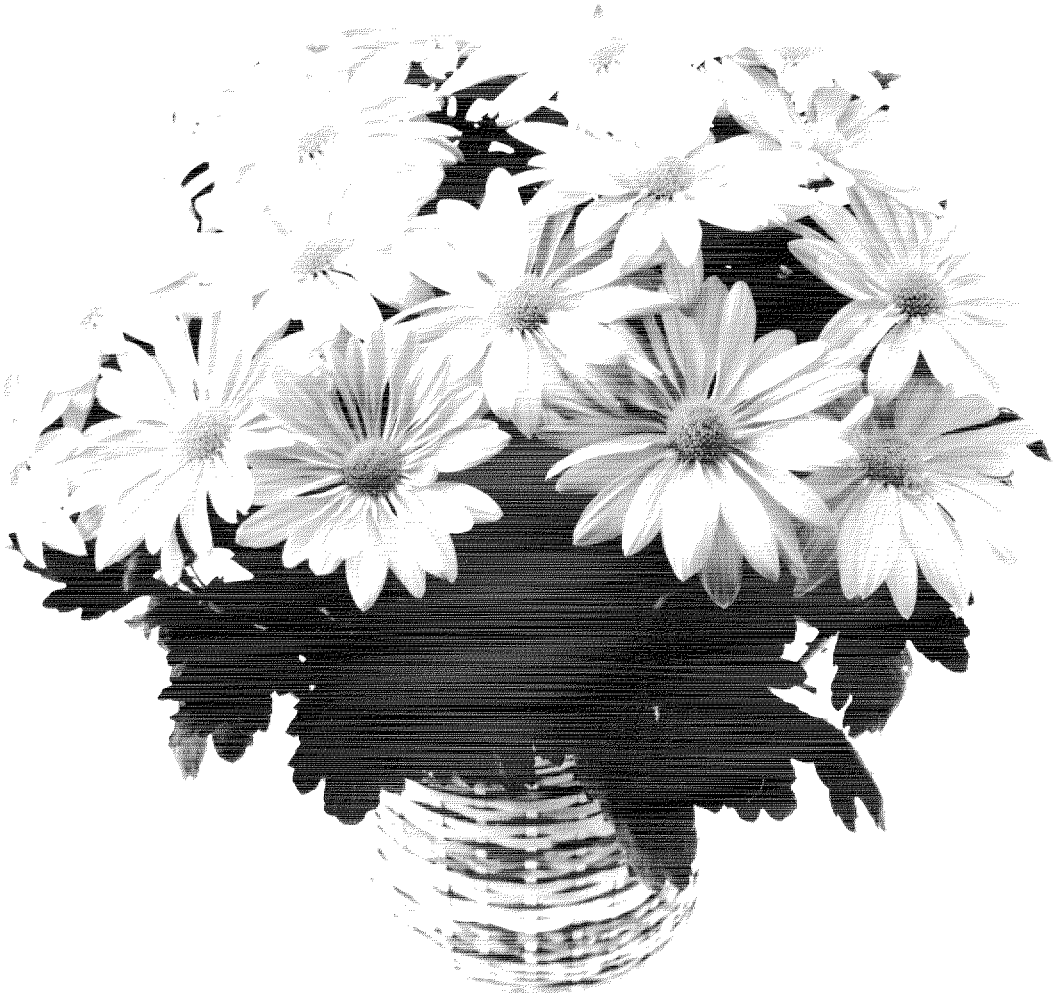

* * * * *